(12) United States Patent
Waldeck (10) Patent No.: US 7,699,055 B2
(45) Date of Patent: Apr. 20, 2010

(54) TRACHEOTOMY CANNULA WITH SHIELD PLATE

(75) Inventor: Franz Waldeck, Nieder-Olm (DE)

(73) Assignee: Tracoe Gesellschaft fur Medizinische Bedarfsgegenstande mbH, Neu-Isenberg (DE)

( * ) Notice: Subject to any disclaimer, the term of this patent is extended or adjusted under 35 U.S.C. 154(b) by 791 days.

(21) Appl. No.: 10/271,929

(22) Filed: Oct. 16, 2002

(65) Prior Publication Data

US 2003/0034036 A1  Feb. 20, 2003

Related U.S. Application Data

(63) Continuation of application No. 09/508,066, filed on Jun. 28, 2000, now abandoned.

(30) Foreign Application Priority Data

Sep. 6, 1997 (DE) .................. 197 39 103

(51) Int. Cl.
*A61M 16/00* (2006.01)
(52) U.S. Cl. .................. 128/207.17; 128/207.14
(58) Field of Classification Search ............ 128/207.17, 128/207.14, 200.26, 912, DIG. 26; 623/9; 604/178

See application file for complete search history.

(56) References Cited

U.S. PATENT DOCUMENTS 2,908,269 A * 10/1959 Cheng .................. 600/237
4,069,826 A * 1/1978 Sessions et al. ............. 604/175
4,392,857 A * 7/1983 Beran .......................... 604/179
4,469,928 A * 9/1984 Wilkinson et al. ............ 219/98
4,832,019 A * 5/1989 Weinstein et al. ...... 128/207.17
5,069,206 A * 12/1991 Crosbie .................. 128/207.17
5,305,742 A * 4/1994 Styers et al. ........... 128/207.17
5,320,097 A * 6/1994 Clemens et al. ........ 128/207.17
5,513,633 A * 5/1996 Islava .................... 128/207.17
5,653,232 A * 8/1997 Rogers et al. .......... 128/207.17
5,813,402 A * 9/1998 Jinotti ................... 128/207.16
5,928,198 A * 7/1999 Lester ................... 604/164.04
6,755,191 B2 * 6/2004 Bertoch et al. ......... 128/200.26

\* cited by examiner

*Primary Examiner*—Darwin P Erezo
(74) *Attorney, Agent, or Firm*—Paul & Paul (57) ABSTRACT

A tracheotomy cannula apparatus with a shield plate is provided for fixedly gripping the cannula with a housing assembly portion of the apparatus. A pair of wing structures form a portion of the apparatus and are attached to the housing assembly, which wing structures assist in holding the cannual apparatus to a patient. The housing assembly includes a housing member through which the cannual is passed. A shield plate is affixed to one side of the housing member, which side is intended to face a patient, and whereby the cannula passing through the housing member also passes through the shield plate. A prestressed spring structure is positioned within a housing member to normally apply pressure against the cannula, thereby holding it in fixed relationship to the housing member. This spring structure has a release actuation member which when operated permits a slide movement of the cannula through the housing member. The wing structures each include an interlocking structural portion, which may be unlocked from each other. This interlocking portion holds the two wing structures in fixed positional relationship to each other when engaged.

26 Claims, 6 Drawing Sheets

TRACHEOTOMY CANNULA WITH SHIELD PLATE

This is a continuation application of U.S. Ser. No. 09/508,066, filed Jun. 28, 2000, now abandoned and claiming the 35 USC 371 priority of International Application No. PCT/DE98/02344 having a filing date of Aug. 8, 1998; and also claiming priority pursuant to 35 USC 119 for this International Application and for Germany Application No. 19739103.6 having a filing date of Sep. 6, 1997.

The present invention concerns a tracheotomy cannula comprising an element in tube or hose form for passing through an incision in the neck and trachea into the trachea of a patient if the upper respiratory tracts of the patient are blocked in order to supply the patient with respiration air through the cannula, and with a shield plate which is mounted to the cannula and the contact of which against the neck of the patient defines the position of the cannula or the end of the cannula in the trachea of the patient.

Tracheotomy cannulae of that kind are used on the one hand in surgery, that is to say, during operations for example in the region of the upper respiratory tracts, but on the other hand also in intensive medicine and finally also for patients whose upper respiratory tracts are permanently blocked because of an illness or an accident and who breathe through such a cannula.

Particularly when cannulae of that kind are intended for prolonged use, that is to say for example in intensive care medicine or for a patient who has to breathe continuously with such a cannula, a certain degree of wearing comfort is of major significance from the point of view of the patient, in order for example to avoid a feeling of pressure, pressure points or wound chaffing and soreness. The position of the shield plate on a tracheotomy cannula is an aspect of significance in that respect insofar as the shield plate serves to define the final position of the tracheotomy cannula at its condition of being inserted into the trachea. In that respect a lower portion of the tracheotomy cannula initially extends substantially perpendicularly along the trachea and then in a relatively gentle curve through about 90° outwardly through the incision in the trachea and the incision in the neck of the patient. It will be appreciated that the anatomical factors involved in the case of the respective patients concerned may be very different, in particular therefore the trachea diameter and the distance of the trachea from the surface of the skin of the neck, as well also as the position of the incisions in the neck and in the trachea.

In order to take account of the varying anatomical factors concerned, there are already tracheotomy cannulae of the most widely varying dimensions and sizes. In that respect in particular the diameter of the tracheotomy cannulae varies, but within certain limits there are also variations in their length and their radius of curvature in the curve which forms the transition from the vertical portion which projects into the trachea to the portion which projects outwardly from the neck of the patient. The shield plate is carried in the region of that curve or at the end of the curve, in which case the tracheotomy cannula is basically inserted into the neck and the trachea of a patient to such an extent that the shield plate bears against the neck of the patient. If however the tracheotomy cannula is selected as being suitable for a patient substantially on the basis of its outside diameter, this still does not mean that the other anatomical factors of the patient are also in conformity with the dimensions which are established by the position of the shield plate. It can therefore certainly be the case that the distance of the trachea of the patient to the surface of the neck is greater or smaller than the distance of the shield plate of the tracheotomy cannula from the vertical portion of the tracheotomy cannula or the notional prolongation thereof. In that case the patient would feel unpleasant pressure or tension forces if the tracheotomy cannula is inserted until the shield plate bears against the surface of the neck.

Admittedly it is in principle also possible to have in store tracheotomy cannulae not only of different diameters but also with different shield plate distances relative to the vertical portion, but this makes storage and also selection and adaptation of a respective tracheotomy cannula for a patient relatively complicated and expensive procedures.

Taking that state of the art as its basic starting point, the object of the present invention is to provide a tracheotomy cannula having the features set forth in the opening part of this specification, which can be adapted in a simple manner to the anatomical factors which obtain in relation to a patient, and which does not cause major expenditure in terms of stocking and adapting tracheotomy cannulae.

That object is attained in that the shield plate of the tracheotomy cannula is mounted to the cannula fixably in various positions in the longitudinal direction of the cannula.

In this case the tracheotomy cannula only needs to be selected in respect of a suitable diameter and is then introduced through the incisions in the neck and trachea of the patient into the neck and trachea thereof. That can possibly also be effected under X-ray monitoring control. When then the cannula has assumed a position which is both suitable in regard to its functional capability and also anatomically correct, insofar as at no point does it exert one-sided pressure or tension forces on the surrounding tissue, the shield plate which is firstly retracted into a position as far away as possible is fixed on the tracheotomy cannula in a position in which it bears against the neck of the patient without in that case the cannula being further pushed into or pulled out of the incision in the neck.

In the preferred embodiment, provided for the shield plate is a clamping device which comes into releasable clamping engagement with the outside of the cannula. Thus, the default condition for the clamping device is to clamp a cannula extending therethrough, with the clamped engagement being releasable. Such a clamping device has the advantage that it can be steplessly secured to the tracheotomy cannulae and that in addition no devices, profiling portions or retaining or detent locations have to be provided on the cannula itself, but rather the cannula can be a substantially smooth tube on which the clamping device is displaced into suitable positions and then clamped fast on the outside surface of the cannula.

In that respect, a preferred embodiment of the invention is one in which the clamping device, as long as it is not actively actuated, is prestressed, i.e., biased, into clamping engagement. This means that the shield plate which is secured on the clamping device retains the position, once adopted, on the tracheotomy cannula, and is displaceable on the cannula only upon actuation thereof, that is to say upon release of the prestressed clamping engagement.

A particularly preferred embodiment of the invention is one in which the clamping device comprises at least two holding portions each having a substantially circular opening through which the tracheotomy cannula is passed, wherein the two holding portions which embrace the cannula are displaceable relative to each other in a direction perpendicularly to the axes of the openings or perpendicular to the axis of the cannula. This means that, when the two openings are for example brought into alignment with each other, they can readily jointly receive the cannula and are displaceable on the outside surface of the cannula, whereas after relative displacement perpendicularly to the axis of the cannula or perpendicularly to the axis of the openings, those openings still partially overlap each other and in the overlap region clamp the cannula fast.

In an alternate embodiment of the invention, it is provided that the at least two holding portions having the openings are pivotable about a third axis which also extends parallel to the axes of the two openings but which is not coincident with one of those axes. When the two portions are pivoted relative to each other about that third axis, the overlap cross-section of the two openings again changes so that in that way it is possible to produce the desired clamping effect. In another alternative configuration the one holding portion is substantially linearly displaceable relative to the other, more specifically once again perpendicularly to the axis of the respective openings or relative to the axis of the cannula.

A particularly preferred embodiment of the invention is one in which the clamping device substantially comprises three portions, wherein two of the portions are fixedly connected together (alternatively they could also be integrally joined together) and jointly form a housing having two mutually aligned openings for a tracheotomy cannula to be passed therethrough, and wherein there is provided a third, substantially flat portion which is accommodated in the housing and which also has an opening for passing a tracheotomy cannula therethrough, which can be at least partially brought into overlapping relationship (alignment) with the two mutually aligned openings of the first and second portions, so that the tracheotomy cannula can extend through all three openings, wherein the third flat portion is prestressed (spring biased) in the housing in such a way that its opening is displaced into a position which is eccentric (out of alignment) relative to the other two openings, whereby the tracheotomy cannula is clamped in the overlapping portion of the three openings by the spring biased pressure operating on the third flat portion and thereby its opening through which the cannula extends.

The two portions forming the housing can for example each have a snap edge and can be fitted together while the third, substantially flat portion is accommodated therebetween or in one of the housing portions. The two housing portions can also be integrally connected together, for s example by a flexural hinge. The multi-part configuration of the housing serves in particular to accommodate the third flat portion securely in the housing formed from the other two portions without it being capable of moving out of the housing.

To produce the eccentric prestressing (spring biased) action, the flat portion preferably has a spring bow which bears against the inside wall of the housing formed by the first and second portions The spring bow can for example comprise a bow which is curved along a circular arc and which is secured with a central part to one end of the flat portion or is integrally connected thereto and has two lateral, forwardly projecting limbs which can be elastically bent away. It will be appreciated that the spring bow can also be a separate portion and can also be in the form of a spring element of another kind.

On the side in opposite relationship to the spring bow, the flat portion preferably has an actuating element which extends outwardly through a lateral opening left free in the housing, so that the actuating element can be pressed in, from the outside of the housing, against the force exerted by the spring bow, wherein the three portions are arranged relative to each other in such a way that, when the actuating element is pressed in, the overlap region of the three openings is increased and possibly the three openings can also be brought completely into mutual alignment so that in that condition the tracheotomy cannula whose outside diameter is slightly smaller than the inside diameter of the three openings can be easily displaced in the three mutually aligned openings or conversely the clamping device can be easily displaced on the tracheotomy cannula. By pressing (moving) the actuating element into the housing, the opening in the fiat portion can be aligned with the openings in the two housing portions. As soon as the actuating element is released however the spring bow urges the central one of the two openings which is disposed on the flat portion arranged in the housing into an eccentric position so that as a result the tracheotomy cannula is clamped.

Desirably the inside edge of the openings of such a device is of a toothed or serrated configuration so that the clamping device provides for a firm fit on the tracheotomy cannula.

As already mentioned, the shield plate of the tracheotomy cannula is secured to the clamping device so that the shield plate is also movable with the clamping device. Desirably, the shield plate is mounted at the side of the clamping device, that is towards the neck of the patient. An actuating device for releasing the clamping device in order to be able to displace it together with the shield plate along the tracheotomy cannula is correspondingly disposed on the clamping device, on the side of the shield plate that is remote from the neck of a patient.

In the preferred embodiment of the invention, the clamping device which is connected to the shield plate of the tracheotomy cannula is of such a design that it can be released with the fingers of a hand and displaced on the tracheotomy cannula. That property is also to be found in the embodiments described in greater detail hereinafter. More specifically, that is achieved in that on the one hand, as already mentioned, the clamping device is connected to the shield plate and on the other hand the clamping device comprises at least two portions which are resiliently prestressed relative to each other and which are prestressed towards each other in the locking direction so that they can be clamped fast on the outside wall of a tracheotomy cannula and which are of such an interconnected configuration and are fitted together in such a way that for example one of the portions of the clamping device projects with respect to other portions so that the two portions can be gripped with the fingers of a hand and the projecting portion can be pushed back, the portions which are prestressed towards each other being released. When handling a tracheotomy tube of that kind, it is often a matter of great significance that either the patient himself or however a doctor or a nurse keeps one hand free, when displacing the shield plate, in order therewith to be able to hold or actuate any other instrument, so that it is a matter of great advantage if the clamping device can be actuated with only a single hand and can be displaced jointly with the shield plate on the tracheotomy tube.

In the preferred embodiment of the invention the shield plate has an opening whose diameter is larger than the diameter of the tracheotomy cannula and also larger than the diameter of the openings of the clamping device, and the shield plate is fitted with its preferably circular opening on to a cylindrical projection of the clamping device, which is arranged substantially concentrically with respect to an adjoining opening of the clamping device for the tracheotomy cannula to pass therethrough.

The cylindrical projection which carries the shield plate preferably has at its end a radially outwardly projecting holding flange.

In addition, in the preferred embodiment of the invention, the shield plate comprises two separate wings which are movable relative to each other and which each have a respective ring portion having an opening and fitted on to the cylindrical projection.

In that case the ring portions, on their mutually facing surfaces, preferably have a tooth configuration or grooving which prevent relative rotation of the ring portions and thus the wings forming the shield plate. It will be appreciated that the relative rotary movement is still to be possible, by overcoming a corresponding resistance force, so that it is possible substantially fixedly to set the wings in the different relative positions which are predetermined by the grooving or toothed configuration.

In that arrangement the ring portions are more or less prestressed into engagement with each other between the holding flange of the cylindrical projection and the base of the cylindrical projection, that is to say the surface of the portion from which the cylindrical projection extends, and they are at any event held together in such a way that they are rotatable relative to each other only when certain holding forces are overcome. In this respect, one of the wings may possibly also be secured to the clamping device or the cylindrical projection in such a way that it is not rotatable with respect to the clamping device so that only the other wing is rotatable relative to the first-mentioned wing and the clamping device and the position of the first-mentioned wing is set together with the clamping device in the desired location.

Further advantages, features and possible uses of the invention will be apparent from the following description of a preferred embodiment and the accompanying drawings in which:

Figure 1:
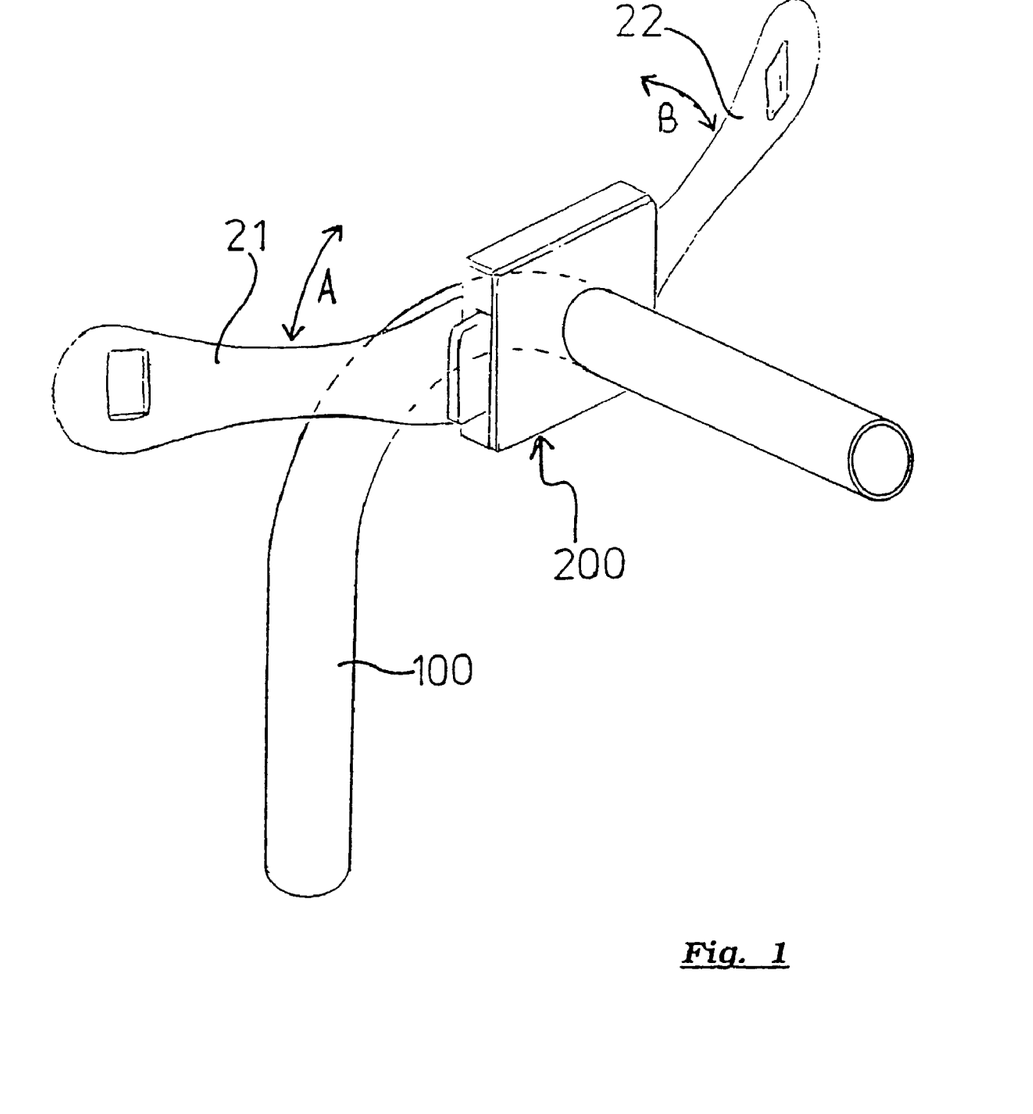
FIG. 1 is a perspective view of a tracheotomy cannula with movable shield plate.

Referring to FIG. 1, shown therein is a tracheotomy cannula 100 with a shield plate in the form of two wings 21, 22 which are secured to a clamping device 200. The clamping device 200 is movable together with the wings 21, 22 on the tracheotomy cannula in the longitudinal direction so that the shield plate 21, 22 can be set into any desired position which is suitable for a patient. In addition the wings 21, 22 are also pivotable about the axis of the tracheotomy cannula 100, as is indicated by the arrows A, B.

FIGS. 2 to 5 show further details of the clamping device 200.

FIGS. 2b and 2c show the clamping device 200 in two different side views which are displaced through 90° relative to each other, while FIG. 2a shows the clamping device in a view which corresponds to the direction of view in FIG. 2b from below as indicated by the arrows IIa, IIa, but with the lower housing portion 2 having been omitted.

Figure 6:
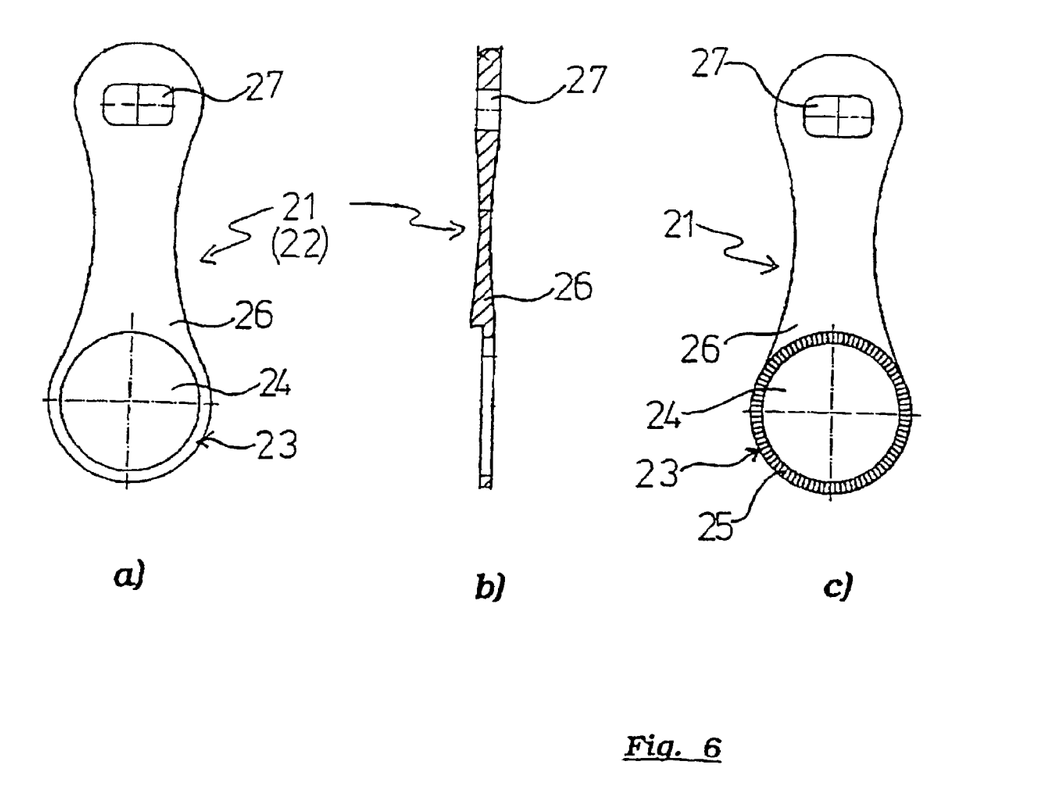
FIGS. 6a-6c shows various views of one of two wings forming a shield plate.

As can be seen by reference to FIGS. 2b and 2c, the clamping device 200 substantially comprises two housing portions 1, 2 which are fitted together, and a flat portion 3 which is inserted therebetween into the housing. The housing portion 1 also has a cylindrical projection 6 with a holding flange 7 so that ring elements 23 which are described with reference to FIG. 6 are received in the intermediate space 8 which is formed between the holding flange 7 and the surface of the housing portion 1, which adjoins the cylindrical projection 6.

FIG. 2a shows a plan view of the flat portion 3 which is inserted into the housing portion 1. In its upper watt which is partially concealed by s the flat portion 3, the housing portion 1 has an approximately circular opening 11 while the flat portion 3 has a corresponding circular opening 13 of the same diameter which however in the illustrated position which corresponds to the rest position of the clamping device 200, is displaced eccentrically with respect to the opening 11. The lower housing portion 2 has a corresponding circular opening 12 which in the assembled condition is aligned with the opening 11 in the upper housing portion 1.

The eccentric position of the opening 13 with respect to the opening 11, which can be seen in FIG. 2a, is brought about by means of a spring bow 4 which is integrally disposed at one end of the flat portion 3 and which bears with its two outwardly and forwardly extending legs against the inside wall of the housing portion 1. Disposed on the side of the flat portion 3, which is in opposite relationship to the spring bow 4, is an actuating tongue or actuating projection 5 which extends through a lateral opening 15 formed by an aperture in the side waif of the housing portion 1. When that actuating projection 5 is pressed into the opening 15, the spring bow 4 elastically yields and the two openings 11, 13 can be brought substantially into alignment. Lateral deflection of the flat portion 3 is prevented on the one hand by the projection 5 being a suitably close fit in the aperture 15 and moreover also by the flat portion 3 being substantially closely fittingly received between the side walls of the housing portion 1. In the view shown in FIG. 2a therefore the flat portion 3 can perform essentially only linear lateral movements in the housing portion 1, in which case the spring bow 4 is prestressed to a greater or lesser degree.

When the projection 5 is not pushed in, the spring stressing effect of the spring bow 4 provides that the tracheotomy cannula which extends simultaneously through the openings 11, 13 and which is of a slightly smaller outside diameter than the openings 11, 13 is clamped by the toothed inside surfaces of the openings 11, 13, whereby the clamping 100 device 200 is substantially immovably held fast to the outside wall of the tracheotomy cannula 100.

Figure 3:
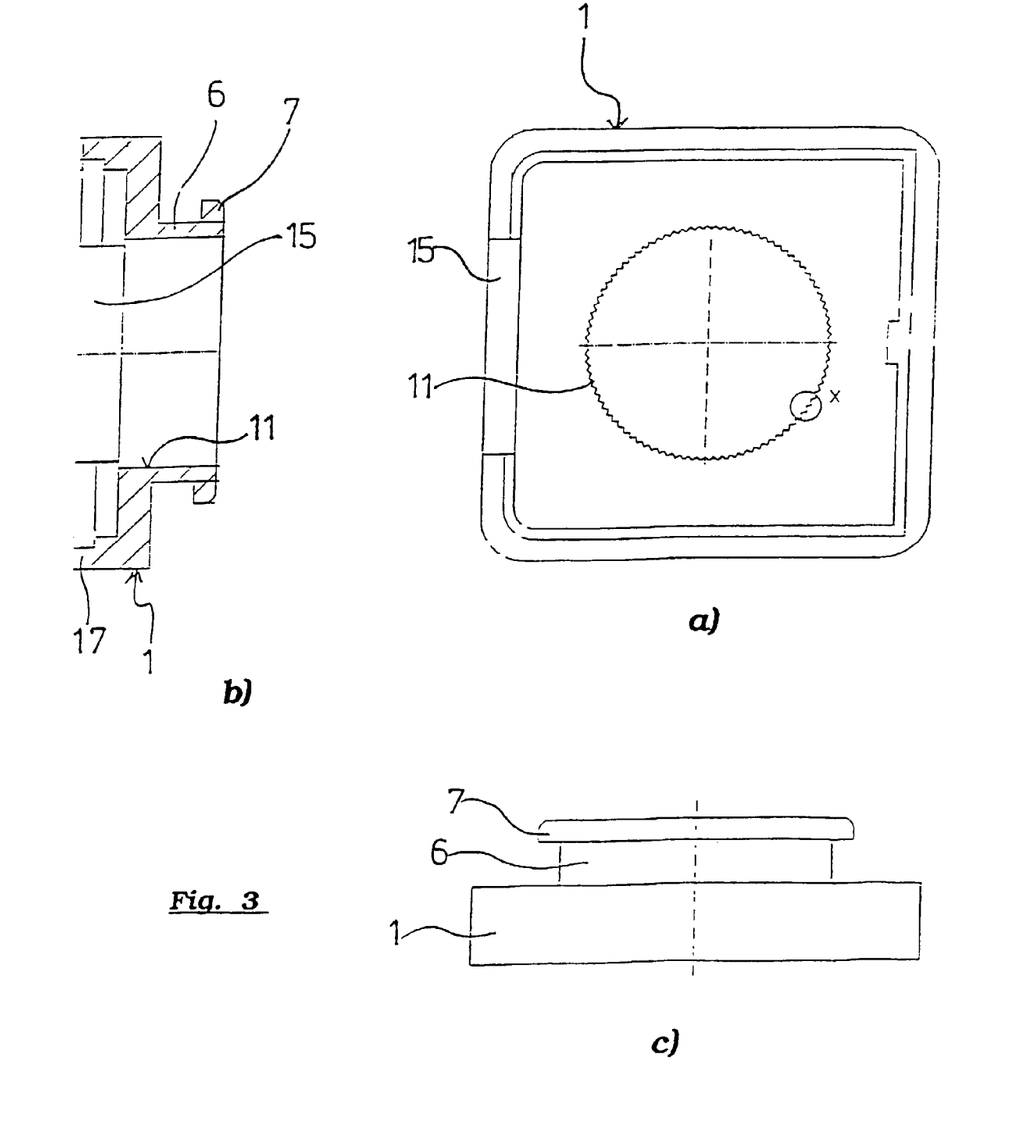
FIGS. 3a-3c shows various views of the first housing portion of the clamping device of FIG. 2.
Figure 4:
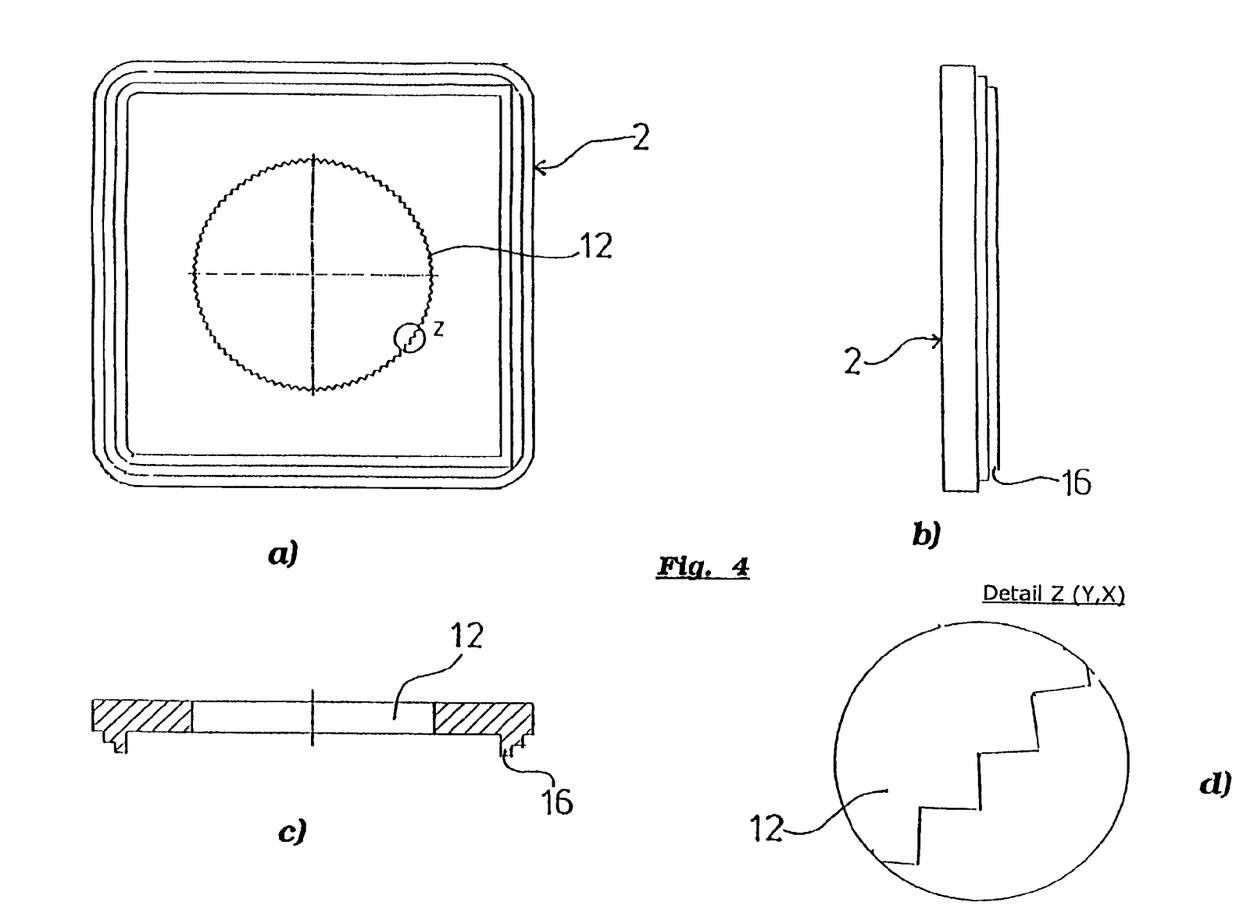
FIGS. 4a-4d shows various views of the second housing portion of the clamping device of FIG. 2.
Figure 5:
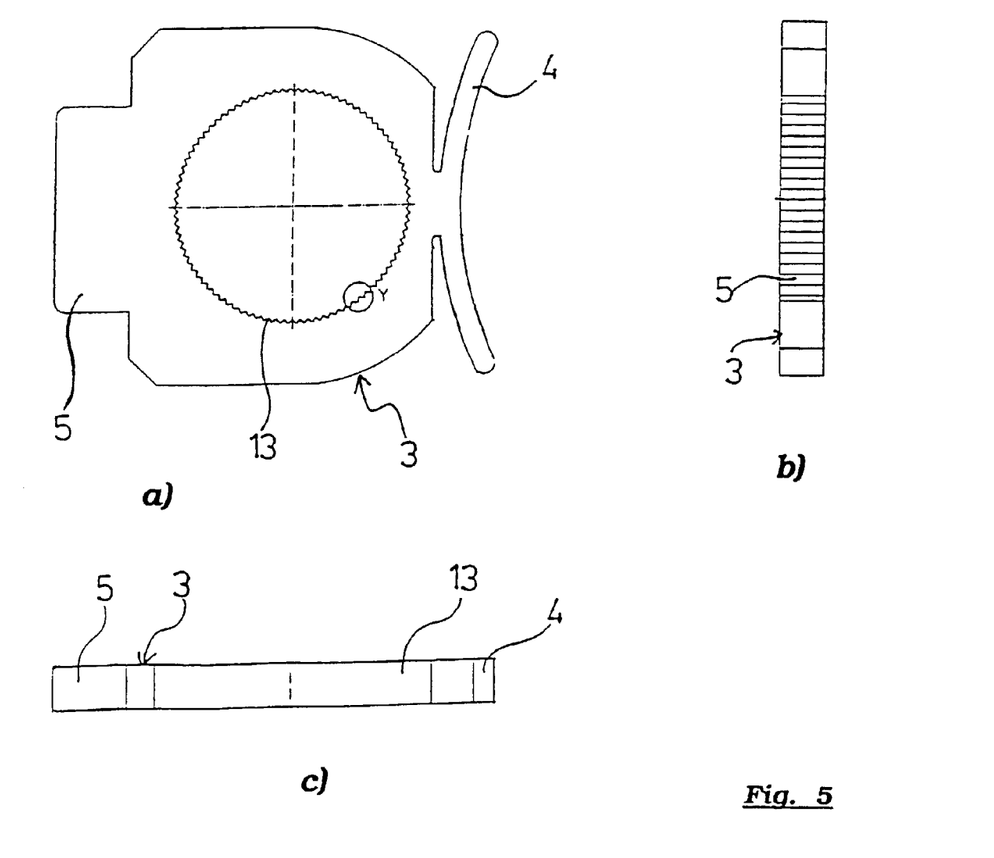
FIGS. 5a-5c shows the third flat portion of the clamping device of FIG. 2.

FIGS. 3 to 5 show the individual parts from which the clamping device 200 is made up, in detail, each in various views.

FIG. 3 shows the upper housing portion 1. It substantially comprises a shallow, rectangular parallelepiped with rounded-off corners, of which a side wall has the above-mentioned aperture 15 for the actuating projection 5 to pass therethrough, and whose upper wall which has the opening 11 is provided with a cylindrical projection 6, at the free end of which a holding flange 7 extends radially outwardly. The cylindrical projection 6 extends concentrically with respect to the opening 11.

As can be seen from the sectional view of FIG. 3b, the side walls of the housing portion 1 are of a stepped configuration so that a correspondingly stepped projection 17 of the housing portion 2 can be assembled in fitting relationship with the side walls of the housing portion 1. FIG. 3c is a view on to the housing portion 1 corresponding to the direction of view from below on to the housing portion 1 shown in FIG. 2a.

Figure 2:
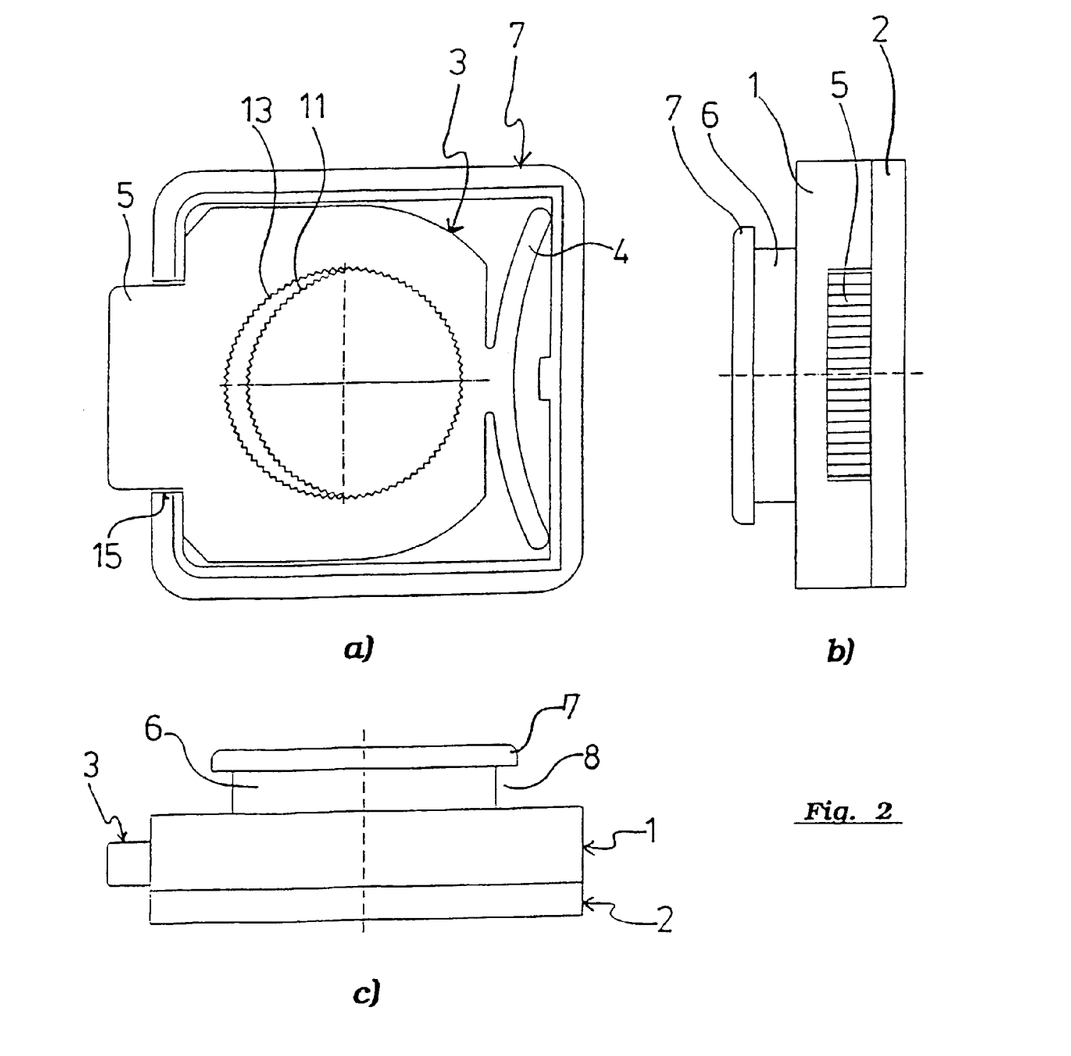
FIGS. 2a-2c shows various views of the clamping device according to the invention.

FIG. 4a shows the lower housing portion 2 in a view from the interior of the housing, FIG. 4b shows a vertical section through the center of the lower housing portion 2 and FIG. 4c shows a side view illustrating the stepped projection 16 whose outside diameter is matched to the inside diameter of the complementary projection 17 on the housing portion 1 so that the two housing portions can be pushed together or fitted together with a tight fit, possibly a press fit, so that they are held together in the form of the housing illustrated in FIG. 2, with the flat portion accommodated therein. FIG. 4d shows a part from the edge of the opening 12, this also precisely corresponding to the details Y and X in FIGS. 3a and 5a. The serrated edge of the opening 12 provides for fixed immovable engagement of the clamping device on the tracheotomy cannula 100.

FIG. 5 shows the flat portion 3 which is accommodated in the housing formed from the portions 1 and 2. The flat portion 3 has an opening 13 of precisely the same diameter as the openings 11 and 12 but it is prestressed by the spring bow 4 in the housing in eccentric relationship with the openings 11 and 12. The shallow actuating projection 5 serves to bring the openings 11, 12 and 13 into a condition of mutual alignment insofar as the spring bow 4 which bears with its ends against the inside wall s of the housing is pressed flat, out of its normally curved position.

FIG. 6 shows one of the two wings 21, 22 which together form the shield plate. These two wings 21, 22 are identical so that only one of these wings needs to be shown here. FIG. 6a shows a rear view of a wing 21, 22, FIG. 6b shows a view of the wing in longitudinal section and FIG. 6c shows a view from the front on to the wing.

The wing 21, 22 is an elongate portion which is approximately boneshaped in plan view, with enlarged ends and a more slender intermediate part, although the wings 21 and 22 respectively are of a relatively flat and thin nature, as can be seen by reference to FIGS. 6b and 6d. The one end is provided with a central opening 24 whose diameter corresponds to the outside diameter of the cylindrical projection 6 of the holding portion 1 of the clamping device. That opening 24 is formed or surrounded by a ring element 23 of which one side is provided with a tooth configuration or grooving 25 which can best be seen from FIG. 6c. In this arrangement the crests of the teeth of the tooth configuration 25 extend substantially radially.

As can also be seen by reference to FIG. 6b, the ring portion 23 of the wing 21 or 22 is only half as thick as the joining part of the wing 21, 22. In this case the tooth configuration or grooving 25 is provided on the side of the ring element 23, which is at the left in FIG. 6b. As can be easily imagined, two such wings 21, 22 which for example face in opposite directions can then be disposed one upon the other with their ring elements in matching relationship, in which case the tooth configurations 25 of the ring elements 23 face towards each other and come into engagement with each other. Because of the stepped transition from the ring element 23 to the adjoining part 26, which is twice as thick, of the wing 21, 22, the shield plate which is made up of the two wings 21, 22 is of a constant thickness throughout, in that region.

As the transition from the thicker part 26 of the wing to the ring element 23 extends only over an angular region of about 90 to 100°, the two wings 21, 22 which are fitted together in matching relationship with their ring elements 23 can also be pivoted relative to each other from their position in which the two wings face in opposite directions, about the common axis of the ring elements, so that they can include with each other an angle of a minimum of 100° and a maximum of 180°. It will be appreciated that the wings 21, 22 can also readily be of such a configuration that they can be pivoted relative to each other over a larger, desired angular region, for example from 0° to 180°.

The two ring elements 23 are fitted on to the cylindrical projection 6 of the housing portion 1, in which case the ring elements are sufficiently stretchable (optionally the flange portion 7 can also be correspondingly deformable or compressible), in order to be able to be moved over the flange portion. The flange portion 7 then holds the two ring elements together so that the tooth configurations 25 remain in sufficiently firm engagement to hold the two wings 21, 22 in a selected angular position, although those wings are also rotatable relative to each other, by applying a certain force, without involving a major degree of difficulty, so that they assume a desired angular position relative to each other.

The other end of the wing 21 also has an opening which is identified by reference 27 and which is provided for passing therethrough and fitting a securing band or ribbon (not shown here).

The invention claimed is:

1. A tracheotomy cannula assembly, comprising:
a cannula for passing through an incision in the neck and trachea;
a shield member through which the cannula extends, which shield member is selectably positionable against the neck of a patient and about the incision there at, being characterized in that the shield member is capable of being selectably fixed to the cannula at various longitudinal locations thereon;
wherein the shield member includes a housing having a plurality of walls forming an enclosure and a clamping device positioned within the housing, the cannula extending through an opening in the housing and being selectably fixed thereto by a selectable operation of the clamping device;
whereof the clamping device also includes a spring biasing member operating to bias the clamping device to engagement with the cannula thereby placing the cannula into clamping engagement with the housing, the spring biasing member having spring portions facing away from each other; and
wherein the clamping device further comprises actuation means for actuation thereof such that by compression of said actuation means in the direction into the housing the clamping engagement is released, wherein the releasing said compression of said actuation means automatically returns said clamping device into engagement with said cannula under the action of said spring biasing member.

2. A tracheotomy cannula according to claim 1 characterised in that the clamping device comprises at least two cannula holding portions each having an annularly configured opening wherein each of which embraces the cannula with at least a portion of the respective annular configuration, wherein the biasing of the clamping device automatically places the annular configurations of each cannula holding portion in contact with the cannula thereby fixing its position against movement.

3. A tracheotomy cannula assembly according to claim 1 characterized in that at least a first one of the holding portions are movable in a direction perpendicular to the longitudinal direction of the cannula.

4. A tracheotomy cannula assembly, comprising:
a cannula for passing through an incision in the neck and trachea;
a shield member through which the cannula extends, which shield member is selectably positionable against the neck of a patient and about the incision there at, being characterized in that the shield member is capable of being selectably fixed to the cannula at various longitudinal locations thereon;
wherein the shield member includes a housing and a clamping device positioned in relation to the housing, the cannula extending through the housing and being selectably fixed thereto by a selectable operation of the clamping device;

whereof the clamping device also includes a spring biasing member operating to bias the clamping device to engagement with the cannula thereby placing the cannula into clamping engagement with the housing; and wherein the clamping device further comprises actuation means for actuation thereof having portions facing away from each other such that by compression of said actuation means the clamping engagement is released;

wherein the clamping device comprises at least two cannula holding portions each of which at least partially embraces the cannula with a respective annular configuration, and wherein the biasing of the clamping device automatically placing the annular configurations of each cannula holding portion in contact with the cannula thereby fixing its position against movement;

wherein the first one of the holding portions is linearly displaceable from being in alignment relative to the second holding portion, upon which linear displacement the first holding portion annular configuration engages the cannula and forces the cannula against the second holding portion annular configuration.

5. A tracheotomy cannula assembly, comprising:

a cannula for passing through an incision in the neck and trachea;

a shield member through which the cannula extends, which shield member is selectably positionable against the neck of the patient and about the incision and being characterized in that the shield member is capable of being selectably fixed to the cannula at various longitudinal locations thereon;

wherein the shield member includes a housing and a clamping device positioned in relation to the housing, the cannula extending through the housing and being selectably fixed thereto by a selectable operation of the clamping device, the clamping device including actuation structure having portions facing away from each other such that by compression of said actuation structure the clamping engagement is released; and whereof the clamping device is biased to engagement with the cannula thereby placing the cannula into clamping engagement with the housing;

further characterized in that the clamping device comprises at least two cannula holding portions each having a respective annular configuration which at least partially embraces the cannula with a respective annular configuration whereof the biasing of the clamping device automatically places the annular configurations of each cannula holding portion in contact with a cannula thereby fixing its position against movement; and also characterized in that at least a first one of the holding portions are movable in a direction perpendicular to the longitudinal direction of the cannula; and further being characterized in that the first one of the holding portions is linearly displaceable from being in alignment relative to the second holding portion, upon which linear displacement the first holding portion annular configuration engages the cannula and forces the cannula against the second holding portion annular configuration; and wherein also being characterized in that the housing is an enclosed structure having a top and bottom walls and side walls, and the clamping device also includes a third holding portion including an annular configuration, wherein the second and third holding portions are formed respectively in the top and bottom walls of the housing with each respectively having an opening being in mutual alignment with one another and of a size to receive the cannula extension therethrough, the second and third holding portions forming the respective annular edges of each respective opening, and also including a substantially flat plate carrying an opening with the first holding portion forming the annular edge of this opening, with the flat plate opening being of a size to receive the cannula extension therethrough, which flat plate opening can be at least partially brought into overlapping relationship with the two mutually aligned openings in the top and bottom walls, wherein the flat plate is prestressed such that its opening is eccentrically displaced with respect to the top and bottom wall openings, whereby the cannula is clamped.

6. A tracheotomy cannula assembly according to claim 5 characterized in that the flat plate and its carried opening are positioned for displacement movement within the housing with the displacement movement being perpendicular to the longitudinal axis of the cannula extension; and also wherein the biasing structure bears against the housing and bears against the flat plate to bias the flat plate to an eccentric displaced position with respect to the top wall opening and bottom wall opening; and characterized in that the releasing of the clamping engagement allows the positioning of the shield along the cannula, and characterized in that the releasing of the compression exerted results again in the engagement of the clamping device on the cannula.

7. A tracheotomy cannula according to claim 6 characterised in that the biasing mechanism is a spring positioned within the housing to bear against an inside wall thereof and against the flat plate, which flat plate has an actuating element for displacing the flat plate from its biased position and thereby compressing the spring.

8. A tracheotomy cannula according to claim 7 characterised in that the annular edges of the housing top and bottom wall openings and the annular edge of the flat plate opening at least in part include a toothed configuration.

9. A tracheotomy cannula assembly according to one of claims 5 to 7 also including an actuating element characterized in that the actuating element is a tongue extending outwardly from an edge of the flat plate in the plane thereof and through a side wall of the housing, and in that the spring is a spring bow extending from the flat plate in the plane thereof on the edge opposite the tongue extension, the spring bow pressing against an adjacent side wall of the housing.

10. A tracheotomy cannula assembly according to claim 9 characterized in that the housing has a slotted side wall through which the tongue extension operates.

11. A tracheotomy cannula assembly according to claim 10 characterized also to include a cylindrical structure which extends outwardly from the bottom wall of the housing the cylindrical structure being positioned surrounding the bottom wall opening; and also including a radially outwardly projecting flange on the outwardly facing end of the cylindrical structure.

12. A tracheotomy cannula assembly according to claim 11 characterized in that the radially projecting flange on the outward end of the cylindrical structure is of a size and shape to cover the tracheotomy opening in a patient and to abut the skin with wearing comfort.

13. A tracheotomy cannula according to claim 9 characterised in that the shield plate comprises two separate wings which are rotatable relative to each other about the cannula.

14. A tracheotomy cannula according to claim 13 characterised in that the wings each are fitted with a respective ring portion which mounts about the outside wall of the cylindrical structure.

15. A tracheotomy cannula assembly according to claim 14 characterized in that the ring portion of each wing is mounted on the cylindrical structure adjacent one another with their mutually facing surfaces having a grooving toothed configuration which prevents relative rotary movement of the ring portions with respect to each other when this configuration is engaged.

16. A tracheotomy cannula assembly according to claim 14 characterized in that the ring portions are each pressed into engagement with each other at a location between the flange and the housing ends of the cylindrical structure.

17. A tacheotomy cannula assembly according to claim 13 characterized in that each wing ring portion is in frictional engagement with the cylindrical structure.

18. A quick release holder and a cannula to be used with a tracheotomy incision, comprising:
a cannula;
a clamping structure for engaging and holding said cannula, said clamping structure being biased to engage and hold said cannula when said cannula extends through the clamping structure;
a spacing structure for positioning said clamping structure away from the skin when said clamping structure engages said cannula, said spacing structure including a skin contacting member extending outwardly peripherally about a clamp engaged cannula and suitable to be seated against the skin and about a tracheotomy incision; and
an activation structure operable against said clamping structure bias for disengaging the clamping structure from said engaging and holding position;
wherein said clamping structure includes:
a housing, having a top wall and bottom wall;
a circular opening in each of said housing top and bottom walls, being in alignment with each other and of a size to easily accept the cannula through said housing; and
a clamping force structure positioned to operate within said housing, said clamping force structure being biased to hold said cannula extending through the housing top and bottom wall circular openings fixed against said top and bottom wall openings by a biasing member.

19. The quick release holder of claim 18, wherein said activation structure engages said clamping structure and is operable from outside said housing.

20. The quick release holder of claim 19, wherein said activation structure extends through a wall of said housing to engage the clamping structure, and is manually operable from outside of the housing.

21. A quick release holder for a tracheotomy cannula, said cannula to be used with a tracheotomy incision, comprising:
a clamping structure for engaging and holding a cannula, said clamping structure being biased to a cannula engaging and holding position;
a spacing structure for positioning said clamping structure away from the skin when said clamping structure engages said cannula, said spacing structure including a skin contacting member extending about a clamp engaged cannula and seatable against and about a tracheotomy incision;
an activation structure operable against said clamping structure bias for disengaging the clamping structure from said engaging and holding position;
wherein said clamping structure includes:
a housing, having a top wall and bottom wall;
a circular opening in each of said housing top and bottom walls, being in alignment with each other and of a size to easily accept the cannula through said housing; and
a clamping force structure positioned to operate within said housing, said clamping force structure being biased to hold said cannula extending through the housing top and bottom wall circular openings fixed against said top and bottom wall openings by a biasing member;
wherein said activation structure engages said clamping structure and is operable from outside said housing;
wherein said activation structure extends through a wall of said housing to engage the clamping structure, and is manually operable from outside of the housing; and
wherein said clamping force structure is a flat plate slidably operable within said housing, said flat plate carrying a circular opening of a size which will easily accept a cannula, and which opening can be aligned with the housing top and bottom wall circular openings for receiving a cannula there through, said plate being movable to press a cannula extending through the plate circular opening against the housing top and bottom circular openings when displaced from alignment with said housing top and bottom circular openings under operation of said spring biasing structure.

22. The quick release holder of claim 21, wherein said spring biasing structure is a spring operating against said flat plate.

23. The quick release holder of claim 22, wherein said activation structure is a tab connected to said flat plate and extending through a wall of said housing, said tab being movable into said housing to move said flat plate against said spring.

24. The quick release holder of claim 23 wherein said spacing structure is a cylinder extending outwardly from said housing bottom wall about the circular opening in the bottom wall, and a rounded enlarged annular flange extending from the outwardly facing end of said cylinder.

25. A quick release holder of claim 24 wherein said holding wings engage said cylinder about its outer wall thereof.

26. The quick release holder 25, wherein said holding wings is a pair holding wings, each said holding wing carrying a cylinder engaging ring on one end, each respective cylinder engaging ring being a step down thickness and carrying a plurality of toothed grooves thereabout on said step down side, said wing pair being capable of engaging said respective ring tooth groove with each other when in proximity abutment, thereby establishing a fixed positional relationship of the pair of wings.

* * * * *

UNITED STATES PATENT AND TRADEMARK OFFICE
CERTIFICATE OF CORRECTION

PATENT NO. : 7,699,055 B2  Page 1 of 1
APPLICATION NO. : 10/271929
DATED : April 20, 2010
INVENTOR(S) : Franz Waldeck It is certified that error appears in the above-identified patent and that said Letters Patent is hereby corrected as shown below:

Abstract, line 5, replace "cannual" with --cannula--
Abstract, line 7, replace "cannual" with --cannula--
Column 1, line 33, replace "chaffing" with --chafing--
Column 3, lines 40-41, replace "for s example" with --for example--
Column 6, line 4, replace "In its upper watt" with --In its upper wall--
Column 6, line 5, replace "partially concealed by s the flat portion" with --partially concealed by the flat portion--
Column 6, lines 19-20, following "against the inside wall of the housing portion 1." Restore missing sentence:
--Disposed on the side of the flat portion 3, which is in opposite relationship to the spring bow 4, is an actuating tongue or actuating projection 5 which extends through a lateral opening 15 formed by an aperture in the side wall of the housing portion 1.--
Column 6, lines 22-23, replace "in the side waif of the housing portion"
with --in the side wall of the housing portion--
Column 7, lines 17-18, replace "with its ends against the inside wall s of the housing" with
--with its ends against the inside wall of the housing--
Column 8, line 53, Claim 3, replace "A tracheotomy cannula assembly according to claim 1" with
--A tracheotomy cannula assembly according to claim 2--
Column 12, lines 46-49, Claim 26, replace "wherein said holdings wings is a pair holding wings," with
--wherein said holding wings is a pair of holding wings--

Signed and Sealed this

First Day of June, 2010

David J. Kappos
*Director of the United States Patent and Trademark Office*